United States Patent
Huber

(10) Patent No.: US 11,579,153 B2
(45) Date of Patent: Feb. 14, 2023

(54) BLOOD UNIT TESTS KIT

(71) Applicant: PRC BIOMEDICAL LTD., Jerusalem (IL)

(72) Inventor: Arie Huber, Haifa (IL)

(73) Assignee: PRC BIOMEDICAL LTD., Jerusalem (IL)

( * ) Notice: Subject to any disclaimer, the term of this patent is extended or adjusted under 35 U.S.C. 154(b) by 426 days.

(21) Appl. No.: 16/326,363

(22) PCT Filed: Aug. 17, 2017

(86) PCT No.: PCT/IL2017/050910
§ 371 (c)(1),
(2) Date: Feb. 18, 2019

(87) PCT Pub. No.: WO2018/033919
PCT Pub. Date: Feb. 22, 2018

(65) Prior Publication Data
US 2021/0055312 A1    Feb. 25, 2021

Related U.S. Application Data

(60) Provisional application No. 62/376,433, filed on Aug. 18, 2016.

(51) Int. Cl.
| | |
|---|---|
| *G01N 33/80* | (2006.01) |
| *G01N 21/64* | (2006.01) |
| *G01N 21/78* | (2006.01) |
| *G01N 33/543* | (2006.01) |
| *G01N 21/77* | (2006.01) |

(52) U.S. Cl.
CPC ......... *G01N 33/80* (2013.01); *G01N 21/6428* (2013.01); *G01N 21/78* (2013.01); *G01N 33/54306* (2013.01); *G01N 33/54366* (2013.01); *G01N 2021/6439* (2013.01); *G01N 2021/7773* (2013.01)

(58) Field of Classification Search
None
See application file for complete search history.

(56) References Cited

U.S. PATENT DOCUMENTS

| | | | |
|---|---|---|---|
| 2007/0042499 A1 | 2/2007 | Schwind et al. | |
| 2009/0035743 A1* | 2/2009 | Minter | G01N 33/80 435/2 |
| 2013/0130298 A1 | 5/2013 | Tarasev et al. | |

FOREIGN PATENT DOCUMENTS

| | | |
|---|---|---|
| CN | 1244919 A | 2/2000 |
| EP | 2 315 024 B1 * | 4/2011 |
| WO | 2015171826 A1 | 11/2015 |

(Continued)

OTHER PUBLICATIONS

Nunes et al;"Red blood cell adherence during 42day hypothermic storage". Cryobiology, 63(3), p. 338.(2011).

(Continued)

*Primary Examiner* — Rebecca M Giere
(74) *Attorney, Agent, or Firm* — Browdy and Neimark, PLLC

(57) ABSTRACT

A diagnostic biological array, kit or system, and method of using same unit for conducting simultaneously blood tests and determining the presence of diseases, the blood type, and blood quality of a blood sample and its applications.

4 Claims, 2 Drawing Sheets

(56) References Cited

FOREIGN PATENT DOCUMENTS

WO      2016113691 A1      7/2016

OTHER PUBLICATIONS

Veale et al; "Effect Of Red Blood Cell (rbc) Storage On Band 3, 4.1 r And Cytoskeletal Proteins". Vox Sanguinis, p. 105, 28. (2013).
Desmonet "imultaneous And Sensitive Detection Of 5 Markers In One Test For Blood Virus Serology". Vox Sanguinis, 107, p. 133. (2014).
De Oliveira et al; "Integrin-associated protein (CD47) is a putative mediator for soluble fibrinogen interaction with human red blood cells membrane". Biochimica et Biophysica Acta (BBA)-Biomembranes, 1818(3), pp. 481-490. (2012).
Lu et al; "Highly multiplexed profiling of single-cell effector functions reveals deep functional heterogeneity in response to pathogenic ligands. Proceedings of the National Academy of Sciences", 112(7), pp. E607-E615. (Jan. 2015).

\* cited by examiner

BLOOD UNIT TESTS KIT

FIELD OF THE INVENTION

The present invention generally relates to diagnostic kits and specifically to a kit that will replace the blood tests that are done to the donated blood unit. The new kits will include blood typing and the presence of contaminating agents and for determining blood condition and quality based on the characters and flow-properties (FP) of the red-blood-cells (RBC).

Blood tests—the future tests of blood when blood donation is processed or when a patient will come for diagnosis, will be done in one procedure and on the same kit array. For blood units, the tests procedure will include all the present tests that are done within the 24 hours of donation. In addition, the kit will measure and score blood quality level and determine the maximal storage period of the specific blood unit.

BACKGROUND OF THE INVENTION

When a person is coming to donate blood, he has to fill up a personal questioner in order to assess his health and the potential risks that can derive from his blood (e.g. Hepatitis C). In addition, the blood bank is running several tests to the donor and to the donated blood. The tests include hemoglobin levels and presence of contaminations (e.g. HIV) in the blood. These tests take around 8-10 hours and are usually done within the first 24 hours after blood donation. These tests are important in order to verify that the donated blood will benefit the recipient and will not harm him.

In many cases, a person receives a blood transfusion because of low levels of iron or hemoglobin. Therefore, it is surprising that in the end of the tests, the blood bank does not mark the levels or the hemoglobin content of the blood unit. Furthermore, it is a common knowledge that men have ~25% more hemoglobin than women.

In addition, in the last few years there are different studies pointing out the quality of packed red blood cells (PRBC) as an important parameter in terms of their survivability and functionality after transfusion. RBC are unique cells that have the ability to go through small capillaries. In order to do that they have to be flexible and should not aggregate (create clusters) or adhere to endothelial cells. In other words, RBC have to have good flow-properties (FP). Inadequate FP of RBC can lead to many problems such as circulatory disorders (e.g. blood pressure) and anemias. Furthermore, if the RBC don't survive the transfusion, the patient dose not receive the hemoglobin content and his body has to deal with cell debris.

Antibodies arrays (protein chip) became a leading tool in biological research. The ability to test the presence and the levels of a certain protein in a sample advanced the understanding of cellular pathways. In addition, the sensitivity of the protein chips is very high and they can detect as low as a few picograms of proteins in a sample. Surprisingly, the use of protein chip is far under use in clinic.

Today, all the tests that are done at the blood bank in order to classify the blood type and the detection of pathogens can be done on a small volume within 2-3 hours. In addition, other tests, such as RBC FP, could be included on the same array and save time and money.

BRIEF DESCRIPTION OF THE INVENTION

The invention includes KIT, system, methods and technologies to perform on the same Biological KIT all the present Blood Bank's tests and other blood quality tests for certain applications. Among the applications will be the maximum storage time of each donated blood unit, comparison between certain blood quality level and other results of scored blood quality.

The present invention provides a novel diagnostic biological kit suitable for simultaneously conducting all blood bank tests and determining quantitative measurable blood quality.

In certain embodiments, the kit of the invention comprises: (a) a glass slide with an array of binding molecules (antibodies and proteins) bound thereon in predefined locations and pattern. The antibodies and proteins are targeting (or are targets of) known molecules (e.g. antibodies against blood type A+). These targets are derived from the RBC/PRBC or serum of the donor/blood unit or the candidate recipient of the blood components; (b) lysis buffer enabling the extraction of proteins of interest from cells; (c) blocking buffer to avoid non-specific binding; (d) wash buffer to avoid non-specific binding; (e) set of conjugated marker-antibodies for specific detection; and (f) manual.

In certain embodiments of the kit of the invention, the quantitative measurable blood quality includes at least one of: (i) maximum storage period of a tested blood unit; (ii) comparison between blood quality of two or more blood units or blood recipients; and (iii) prediction of transfused survivability of PRBCs.

In certain embodiments of the kit of the invention, the quantitative measurable blood quality comprises: (i) data regarding RBCS' deformability; (ii) RBCS' aggregability; (iii) RBCS' adherence to endothelium; (iv) RBCS' inventory management including maximum storage period; and/or (v) the prediction of RBCS' survivability after transfusion.

In certain embodiments of the kit of the invention, the blood bank tests comprise at least one of: blood type, blood sub-group, identification of contaminating agents, and any combination thereof. In specific embodiments, the contaminating agents are indicative of HIV, hepatitis, syphilis, Zika, or other elements (e.g. prions) that might influence the transfused patient, or any combination thereof.

In certain embodiments of the kit of the invention, the binding molecules are peptides, enzymes, proteins, antibodies or antibody binding fragments and other methods (e.g. heptamers, biotin-streptavidin, electric charge) that bind specifically to antigens present in the blood sample or that can measure it. In alternative embodiments, the binding molecules are peptides, enzymes, proteins, antigens, antibodies or antibody binding fragments and other methods (e.g. heptamers, biotin-streptavidin, electric charge) that bind specifically to antibodies present in the blood sample or that can measure it.

The present invention further provides a diagnostic system comprising: (a) the novel diagnostic biological kit according to the invention for detection of target molecules and conducting blood tests; (b) a scanner that detects fluoresce or chemiluminescence light source; (c) a detector positioned to detect light reflected, color change (or even electric charge) from the surface of the array, and thereby determine specific binding of target molecules to the array surface, wherein interference of reflectance of light illuminating the array's surface occurs due to specific binding of target molecules thereto, which is detectable by said light detector; and (d) a computing system comprising a processor and memory, designed to receive data regarding interference of reflected light, determining therefrom the presence or absence of target molecules within a tested blood sample, and quantitative and measurable blood quality, wherein said computing system uses an algorithm that determines expression levels of the target molecules according to the location of the light signals, and present results of said blood tests.

In certain embodiments of the kit and system of the invention, the quantitative and measurable blood quality is determined by using blood tests and parameters correlating to RBC flow property (FP).

In certain embodiments of the kit and system of the invention, all the blood tests are performed simultaneously on the same array. In certain embodiments, the blood tests are indicative of various diseases and conditions associated with RBCS' defects (e.g. anemia).

In certain embodiments, the kit and system of the invention are used for determining at least one of: (i) the presence of various diseases; (ii) blood type; (iii) the maximum storage period of specific blood unit; (iv) predication of survivability of transfused RBC (v) measurable blood unit quality for any comparison; and (vi) match between two or more blood units or samples, and any combination thereof.

The present invention further provides a method for determining quantitative and measurable blood quality, said method comprising: (a) contacting a blood sample with a diagnostic biological kit of the invention under conditions that permit specific binding of target molecules to the binding molecules within said array; (b) detecting light reflected off the surface of the array under conditions effective to identify any target molecules bound thereto, thereby determining the presence of said target molecules within said blood sample; (c) determining, based on said light reflection data, whether a target molecule is present or absent from the tested blood sample; and (d) determining quantitative and measurable blood quality based on the above determinations.

In certain embodiments, the method of the invention further comprises step (a1) of washing the array to remove materials/molecules un-specifically bound thereto.

In certain embodiments of the method of the invention, the light detection step comprises (i) measuring light reflected from the array and providing an output identifying specifically bound target molecules based on the measured reflected light; and/or (ii) measuring color change within the array and providing an output identifying specifically bound target molecules based on the measured change of intensity of the signal.

In certain embodiments of the method of the invention, the measuring of the reflected light further comprises capturing an image of at least a substantial portion of the surface of the array.

BRIEF DESCRIPTION OF THE FIGURES

For better understanding of the invention and to show how the same may be carried into effect, reference will now be made, purely by way of example, to the accompanying figures.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the figures making apparent to those skilled in the art how the several forms of the invention may be embodied in practice.

In the accompanying figures:

FIG. 1 is a schematic representation of a workflow for using a protein chip of the invention.

FIG. 2 illustrates a gasket used for separating arrays according to some embodiments of the invention.

DETAILED DESCRIPTION OF THE INVENTION

Figure 1:
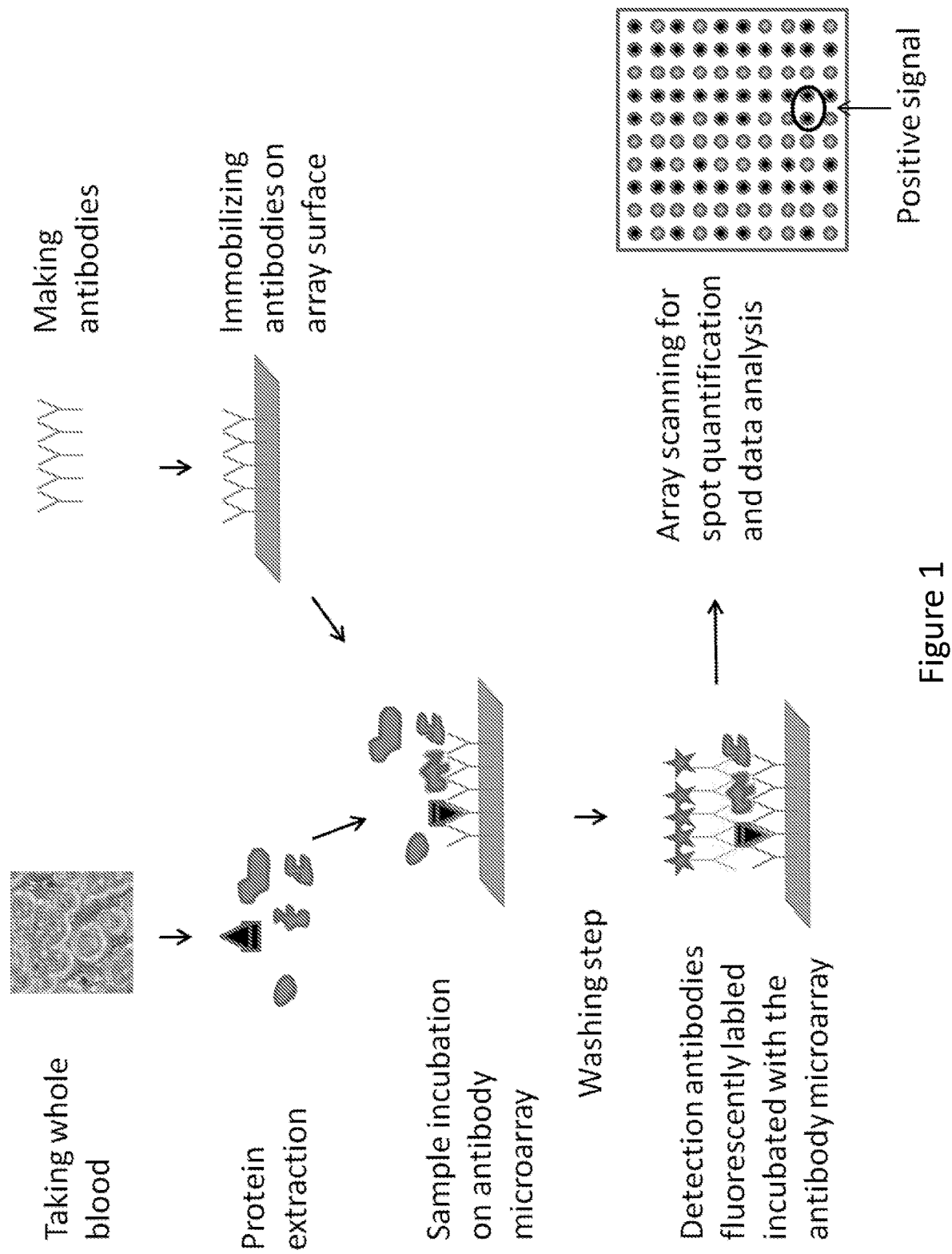

Before explaining at least one embodiment of the invention in detail, it is to be understood that the invention is not limited in its application to the details of construction and the arrangement of the components set forth in the following description or illustrated in the figures. The invention is applicable to other embodiments or of being practiced or carried out in various ways. Also, it is to be understood that the phraseology and terminology employed herein is for the purpose of description and should not be regarded as limiting.

The methods aim to include blood bank tests, including blood quality and maximum storage period, on the same blood sample, same kit panel and same process, by using dedicated antibodies to each test type, wherein each type of said dedicated antibodies has no impact on other test types, by addressing antibodies calibration for each test type.

The blood quality and its maximum storage period are determined by the red blood cell ("RBC") characters and it's scored flow properties (FP). RBC's characters and FP are mainly measured by: (i) RBC deformability—cells' ability to adapt their shape to minimize their resistance to flow, particularly in the capillaries; (ii) RBC self-aggregability—cells' tendency to form multi-cellular aggregates under low-flow states or damage to RBC; and (iii) RBC adherence—cells' potential to adhere to the blood vessel wall endothelial cells.

The quality of blood and its derived applications is influenced from the cells that have low flow properties (FP). The percentage of low FP in the RBC population has to be low, and we have gained the experience in setting the threshold of low FP RBC and their effect on the whole RBC population. Thus, the FP can be characterized by certain measurable characterizations and behavior of (virtually) an individual RBC that impact RBC FP including their elasticity/flexibility, adhesion and aggregation. In addition, It is critical (and so it was set by the FDA) that at least 75% of the transfused RBC will survive after 24 hours from transfusion. In fact, in many cases the survivability percentage is lower.

The FP determine the survivability rate, and FP deterioration over time (e.g. during storage) occurs in a predictive and measurable way. Therefore, current FP (which is very different among people/donors) determines the effective (maximal) storage duration (that will still yield 75% survivability). In addition, the FP of the donated blood should be at least as good as the FP of the recipient, otherwise it can cause more harm than benefit to the blood circulation of the recipient, especially in the periphery (microcirculation).

The present invention provides a sensitive and reliable method and kit comprising a novel biological array, for classifying the blood units in regards to the blood type and the presence of pathogenic agents and determining blood quality by testing measurable RBC characteristics and their FP.

Thus, the present invention provides a method for running all the above mentioned tests, and others, on one array, the method comprising: (a) obtaining a whole blood sample; (b) lysing the cells and extracting proteins therefrom; (c) subjecting the lysates with selected antibodies; (d) determining blood type, presence of contamination, and blood quality; and (e) determining blood maximum storage period and blood quality comparison.

The device, method and kit of the present invention enable to predict the survivability percentage of RBC within the 24 hours following blood transfusion, the maximum storage period of a blood unit after donation (that will assure, e.g., the survivability of at least 75% of the transfused RBC within 24 hours). Furthermore, the present invention provides an improvement in blood flow (especially in the periphery) in people receiving blood transfusion by monitoring the transfused blood's RBC flow property (FP). Furthermore, the present invention provides an improvement in detecting diseases and other condition of the blood sample.

Example of a kit algorithm and process:
1. Protein extraction from the blood sample. Done by lysing the RBC (e.g. hypotonic pressure).
2. Blocking the antibodies array (e.s. with BSA). The antibodies array chip is a glass slide with antibodies attached thereto by any suitable technique. The antibodies correspond to the antigens of interest (e.g. blood type A).
3. When a sample of RBC lysate is placed on said chip, the proteins of interest bind to their corresponding antibodies.
4. A good wash of the slide will clear away the other (irrelevant) proteins from the slide, which did not bind to the antibodies.
5. Another set of specific antibodies (or heptamers), capable of binding to another epitope of the proteins of interest is used for higher specificity. These antibodies are conjugated to a fluorophore that can be read/detected by a florescent reader.
6. A good wash of the slide will clear away the non-binded antibodies.
7. The induced signal is converted to numbers by the computer associated with the reader. The computer uses an algorithm that converts the numbers into a chart that is clear to the reader in terms of the tested parameters. When a protein is expressed more in the tested sample, more specific antibodies will bind to it and will induce a higher signal.
8. It will be appreciated by persons skilled in the art that the present invention is not limited to what has been particularly shown and described hereinabove. Rather the scope of the present invention is defined by the appended claims and includes combinations and sub-combinations of the various features described hereinabove as well as variations and modifications thereof, which would occur to persons skilled in the art upon reading the foregoing description.

FIG. 1 is a schematic representation of the workflow for using the above exemplified antibodies array and method of the present invention: Each antibody is calibrated for its best concentration in order to yield a good and stable signal (e.g. working curve according to Michaelis Menten). The antibodies are added to the BB-kit array of the invention under validation of high specificity (e.g. in an ELISA format) and without cross-contamination. The antibodies are tested for their stable binding to the glass slide.

Workflow (as in FIG. 1): Once the kit is ready, there is a need to block the antibodies with general buffer containing proteins (e.g. BSA). A whole blood sample is taken from the donor/recipient, or PRBC from a blood unit and subjected to a lysis buffer (the lysis buffer enables a better extraction of the proteins), then the lysate can be placed on the BB-kit array of the invention. The proteins bind to the corresponding antibodies. A washing step is applied in order to remove the other proteins in the sample. Another set of corresponding antibodies is incubated. The antibodies find their targets (same protein as the lower antibody, as part of the sandwich, but targeting another epitope). A washing step is applied in order to remove the antibodies that didn't find their corresponding proteins. The array is then scanned by a designated scanner that can quantify the intensity of the fluorophore that is conjugated to the antibodies. A computer utilizes an algorithm for the array that convert the numbers into a result (e.g. blood type "A$^+$").

Figure 2:
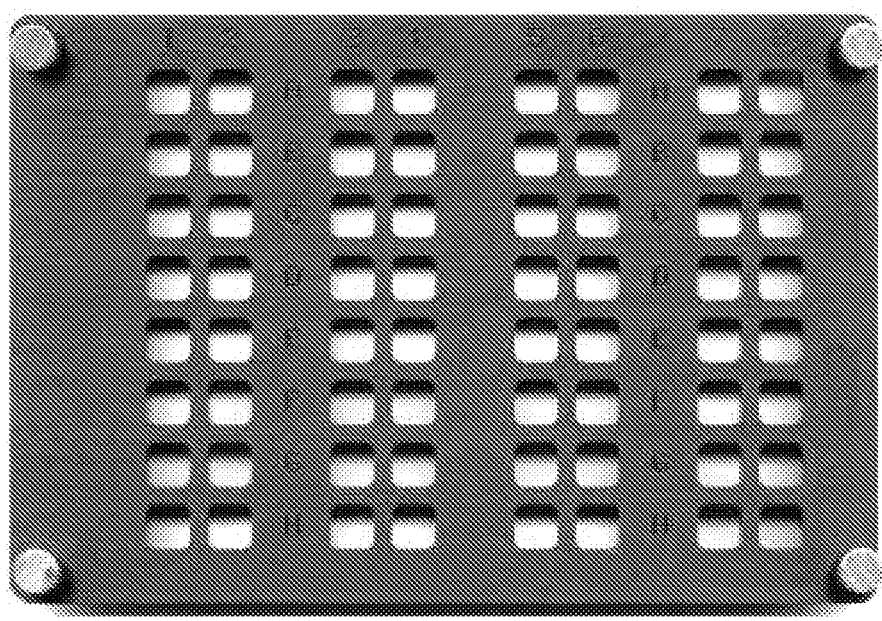

The glass slides used in the BB-kit of the invention can contain a few arrays. In order to avoid cross contamination between samples and arrays, it is needed to separate the arrays. The gasket shown in FIG. 2 is used to separate 16 different arrays on 4 different slides.

In certain embodiments, the method of the invention further comprises a preliminary calibration step for each antibody for performing the test(s) in a good manner (e.g. creating a working curve according to Michaelis Menten), followed by a step of adding said antibodies to the array under validation of high specificity and without cross-contamination.

In certain embodiments, there is a need to calibrate each antibody in an ELISA format and then to print them on a chip.

In this stage the technical issues of utilizing the antibodies in an array format are tested. The antibodies are then being tested for their performance on the same array, that they attached well to the slide and which slide is the best. Then the antibodies are calibrated for their optimal working concentration, and that the reading is good and stable.

A unified kit of the invention, also known as BB-kit, is based on known factors that are routinely checked in the blood bank. Some of these tests (e.g. blood typing) are done both on the donor's blood and on the recipient's blood. Most of these tests are done by utilizing antibodies against known targets such as blood typing; e.g., the surface of red blood cells (RBC) in Type A blood has antigens known as A-antigens. When there is a matching between a blood unit and a recipient there is a screening for the presence of antibodies in the recipient's blood against sub-typing of donor's blood (e.g. M, N & S).

There are identified targets that are important for the characterization of RBC and to the assessment of their quality mainly in regard to their ability to survive and to function after transfusion.

This BB-kit of the invention will replace all the antibodies-based-assays that are done today in the blood bank by assembling all the antibodies for blood typing, contaminating agents, presence of antibodies and RBC characteristics into one big antibody array chip.

The protein chip of the invention is a very powerful tool for diagnostics with a very high specificity, enabling to measure all the components of a blood sample in one quick array.

Kit specifications according to specific embodiments of the invention can be, e.g.:

| | |
|---|---|
| Protein Chip Kit characters | The kit is targeting approximately 50 proteins
The kit is targeting a few housekeeping genes (i.e. GAPDH).
The Kit can deal with whole cell lysate
The array is functioning as an indirect ELISA (sandwich).
The chip is transparent enabling reading by as many readers as possible.
The $2^{nd}$ set of antibodies are conjugated to a fluorophore without the need for another set of antibodies (commonly termed secondary's)
Different algorithms with different specifications are determined according to the application (e.g. storage period, survivability and microcirculation).
The chip has a positive and negative controls in addition to the IgGs.
The kit can deal with low expression levels (e.g. lower than 10 ng) of protein.
The chip is highly sensitive and accurate (less than 1% error).
The kit has can deal with high variety of expression levels of the different proteins and has a standard curve for every target on the chip. |
| The kit components | The whole kit contains:
1. Protein Chip.
2. Lysis Buffer - vial A.
3. Blocking Buffer - Vial B
4. Wash Buffer - vial C.
5. Set of conjugated antibodies - vial D.
6. Manual. |
| $1^{st}$ stage test process | Measure the quality of the RBC in the blood unit/sample (before transfusion) as an indication for the transfusion's matching and outcome (e.g. Blood type & RBC survival after 24 hours).
Processing the blood samples:
a) Take a blood sample (1 ml).
b) Add 4 ml PBS.
c) Mix and centrifuge (4° C., 200 g for 5 minutes).
d) Aspirate supernatant.
e) Take 150 µl from RBC into a new Eppendorf tube.
f) Add 1 ml PBS.
g) Mix and centrifuge (4° C., 200 g for 5 minutes).
h) Aspirate supernatant.
i) Add 300 µl lysis-buffer (vial A) and vortex well.
j) Incubate sample on ice for 10 minutes and vortex from time to time.
Sample processing should start within 30 minutes after drawing out from the blood unit/sample.
Processes samples with the chip according to the protocol in the manual.
The whole process will not exceed 2 hours. |

Example of KIT Array Structure

| | | Concentration | | | | | Control | Concentration | | | | |
|---|---|---|---|---|---|---|---|---|---|---|---|---|
| | IgG | 1 | 2 | 3 | 4 | 5 | DDW | 1 | 2 | 3 | 4 | 5 |
| | A | 1 | 2 | 3 | 4 | 5 | PBS | 1 | 2 | 3 | 4 | 5 |
| | B | 1 | 2 | 3 | 4 | 5 | PBS | 1 | 2 | 3 | 4 | 5 |
| Sub group | Rh (D, C, E, c, e, $C^w$) | 1 | 2 | 3 | 4 | 5 | BSA | 1 | 2 | 3 | 4 | 5 |
| | Duffy ($Fy^a$, $Fy^b$) | 1 | 2 | 3 | 4 | 5 | | 1 | 2 | 3 | 4 | 5 |
| | Kell (K, k, $Kp^a$, $Kp^b$, $Js^a$, $Js^b$) | 1 | 2 | 3 | 4 | 5 | DDW | 1 | 2 | 3 | 4 | 5 |
| | Kidd ($Jk^a$, $Jk^b$) | 1 | 2 | 3 | 4 | 5 | PBS | 1 | 2 | 3 | 4 | 5 |
| | Lewis ($Le^a$, $Le^b$) | 1 | 2 | 3 | 4 | 5 | PBS | 1 | 2 | 3 | 4 | 5 |
| | P (P1) | 1 | 2 | 3 | 4 | 5 | PBS | 1 | 2 | 3 | 4 | 5 |
| | M, N, S, s | 1 | 2 | 3 | 4 | 5 | PBS | 1 | 2 | 3 | 4 | 5 |
| | Luth ($Lu^a$, $Lu^b$) | 1 | 2 | 3 | 4 | 5 | PBS | 1 | 2 | 3 | 4 | 5 |
| | $Xg^a$ | 1 | 2 | 3 | 4 | 5 | PBS | 1 | 2 | 3 | 4 | 5 |
| Contaminating agents | HIV* | 1 | 2 | 3 | 4 | 5 | BSA | 1 | 2 | 3 | 4 | 5 |
| | Hepatitis* | 1 | 2 | 3 | 4 | 5 | BSA | 1 | 2 | 3 | 4 | 5 |
| | Syphilis* | 1 | 2 | 3 | 4 | 5 | | 1 | 2 | 3 | 4 | 5 |
| RBC Quality/derived maximum storage period | Factor-1 | 1 | 2 | 3 | 4 | 5 | | 1 | 2 | 3 | 4 | 5 |
| | Factor-2 | 1 | 2 | 3 | 4 | 5 | | 1 | 2 | 3 | 4 | 5 |
| | Factor-3 | 1 | 2 | 3 | 4 | 5 | | 1 | 2 | 3 | 4 | 5 |
| | IgG | 1 | 2 | 3 | 4 | 5 | DDW | 1 | 2 | 3 | 4 | 5 |

*Presence of antibodies (in the serum) against contaminating agents.

The BB-kit of the invention is based, for the most part, on known factors that are routinely checked in the blood bank. Some of these tests (e.g. blood typing) are done both on the donor's blood and the recipient's blood. Most of these tests are done by utilizing antibodies against known targets such as blood typing; For example, the surface of red blood cells (RBC) in Type A blood has antigens known as A-antigens. When there is a matching between a blood unit and a recipient there is a screening for the presence of antibodies in the recipient's blood against sub-typing of donor's blood (e.g. C, E & K).

The present invention has identified targets that are important for the characterization of RBC and to the assessment of their quality mainly in regard to their ability to survive and to function after transfusion.

The BB-kit of the invention replaces all the "antibodies-based-assays" that are done in the blood bank by assembling all the antibodies for blood typing, utilizing recombinant proteins in order to find the presence of antibodies (in the serum) for contaminating agents. In addition, the RBC characteristics will be assayed on the same array with antibodies that reflect the changes in the RBC flow-properties.

The protein chip of the invention is a very powerful tool for diagnostics with a very high specificity, enabling to measure all the components in one array.

The BB-KIT of the invention further comprises: (a) a glass slide with an array of antibodies and proteins that are glued to it in specific and known locations. The antibodies and proteins are targeting (or are targets of) known molecules (e.g. antibodies against blood type A+). These targets are derived from the RBC/PRBC or serum of the donor/blood unit or the candidate recipient of the blood components; (b) lysis buffer-enabling the extraction of the proteins of interest (e.g. blood type B+); (c) blocking buffer- to avoid non-specific binding; (d) wash buffer- to wash away proteins and other molecules that were non-specific bound; (e) set of conjugated antibodies—for specific detection; and (f) manual.

The RBC/PRBC contains (or not in the case of negative, e.g. "A⁻") the proteins of interest: When the RBC lysates are placed on the BB-kit array of the invention, the proteins bind to their corresponding antibodies/proteins; Washes move away any proteins that didn't find a target; Detection antibodies (conjugated to a fluorophore (e.g. Alexa 647)) can bind to the corresponding protein in another epitope; After another wash for removing unbound detection antibodies, the array is visualized in a designated device that can measure the intensity of the fluorescent signal. According to the location of the signal, an algorithm converts the signal into an expression level of the targets of interest.

A serum contains the proteins (antibodies) of interest: When the serum is placed on the BB-kit array of the invention, the antibodies bind to their corresponding proteins; Washes move away the antibodies and proteins that didn't find any target; Detection antibodies (conjugated to a fluorophore (e.g. Alexa 647)) can bind to these antibodies; After another wash the array is visualized in a designated device that can measure the intensity of the fluorescent signal; According to the location of the signal, an algorithm converts the signal into the presence and expression level of the targets of interest.

The present invention provides a diagnostic biological array and/or kit (BB-kit) suitable for simultaneously conducting multiple blood bank tests, said array comprising a substrate comprising a surface with binding molecules bound thereon, wherein said substrate is divided into regions such that each region comprises binding molecules that bind the same or different target molecule or cells, wherein binding of a target molecule to said binding molecules causes a detectable change in light reflectance at the binding region, which is indicative of the presence of said target molecule in the tested blood, and wherein said array is further used for determining quantitative and measurable blood quality.

In certain embodiments of the array and BB-kit of the invention, the quantitative and measurable blood quality comprises: (i) data regarding red blood cells' (RBCS') deformability; (ii) RBCS' aggregability; and/or (iii) RBCS' adherence to endothelium; and/or (iv) RBCS' maximum storage period. In specific embodiments, said quantitative and measurable blood quality is determined by using blood tests and parameters correlating to RBC flow property (FP).

In certain embodiments of the array and BB-kit of the invention, the blood bank tests comprise any one of: blood type, blood sub-group, identification of contaminating agents, and any combination thereof.

In certain embodiments of the array and BB-kit of the invention, the contaminating agents are indicative of HIV, hepatitis, and/or syphilis.

In certain embodiments of the array and BB-kit of the invention, the binding molecules are peptides and/or antibodies or antibody binding fragments that bind specifically to antigens present in the blood sample. Alternatively, said binding molecules are peptides and/or antigens that bind specifically to antibodies present in the blood sample.

The present invention further provides a diagnostic kit comprising: (a) a diagnostic biological array or kit (BB-kit) suitable for simultaneously conducting multiple blood bank tests for detection of target molecules and conducting blood tests; (b) reagents; and (c) instruction manual, wherein the kit is designed to identify the presence or absence of target molecules in a tested blood sample, and determine therefrom quantitative and measurable blood quality.

In certain embodiments, the diagnostic system of the invention comprises: (a) a diagnostic biological array according to the invention for detection of target molecules and conducting blood tests; (b) a light source that is positioned to illuminate said array; (c) a light detector positioned to detect light reflected (and/or color change) from the surface of the array, and thereby determine specific binding of target molecules to the array surface, wherein interference of reflectance of light illuminating the array's surface occurs due to specific binding of target molecules thereto, which is detectable by said light detector; and (d) a computer comprising a processor and memory, designed to receive data regarding interference of reflected light, determining therefrom the presence or absence of target molecules within a tested blood sample, and quantitative and measurable blood quality.

Notably, all the blood tests are performed simultaneously on the same array/BB-kit of the invention. In certain embodiments, said blood tests are indicative of various diseases and conditions associated with RBCS' defects (e.g. anemia).

In certain embodiments, the BB-kit of the invention is used for determining at least one of: (i) the presence of various diseases; (ii) blood type; (iii) the maximum storage period of specific blood unit; (iv) measurable blood unit quality for any comparison; and (v) match between two or more blood units, and any combination thereof.

The present invention further provides a method for determining quantitative and measurable blood quality, said method comprising: (a) contacting a blood sample with an array/BB-kit of the invention under conditions that permit specific binding of target molecules to the binding molecules within said array; (b) detecting light reflected off the surface of the array under conditions effective to identify any target molecules bound thereto, thereby determining the presence of said target molecules within said blood sample; (c) determining, based on said light reflection data, whether a target molecule is present or absent from the tested blood sample; an (d) determining quantitative and measurable blood quality based on the above determinations.

In certain embodiments, the method of the invention further comprises step (b1) of washing the array to remove materials/molecules un-specifically bound thereto.

In certain embodiments of the method of the invention, the light detection step comprises: (i) measuring light reflected from the array and providing an output identifying specifically bound target molecules based on the measured reflected light; and/or (ii) measuring color change within the array and providing an output identifying specifically bound target molecules based on the measured change of color. In specific embodiments, measuring the reflected light further comprises capturing an image of at least a substantial portion of the surface of the array.

The present invention also provides a method for determining quantitative and measurable blood quality, said method comprising: (a) providing a diagnostic biological array according to the invention or a diagnostic kit or system according to the invention; (b) screening a blood sample for the presence or absence of target molecules; and (c) making a diagnosis based upon the result of said screening, and determining quantitative and measurable blood quality.

The invention claimed is:

1. A method for determining quantitative and measurable blood quality in a single test, said method comprising:
  a) contacting a blood sample with a diagnostic biological kit suitable for simultaneously conducting various blood bank tests under conditions that permit specific binding of target molecules to binding molecules within an array, wherein said kit comprises: a dot-spot array of binding molecules selected from the group consisting of antibodies, proteins and peptides bound thereon in predefined locations and pattern; lysis buffer; blocking buffer; and wash buffer, wherein said blood bank tests comprise determination of quantitative and measurable blood quality, blood type, blood sub-group, and identification of contaminating agents, wherein said quantitative and measurable blood quality are based on specific red blood cell's (RBCs') characteristics and comprises data regarding: (i) RBCs' deformability; (ii) RBCs' aggregability; and (iii) RBCs' adherence to endothelium, and comprises: (iv) maximum storage period of a tested blood unit; (v) prediction of functionality of transfused RBCs; and (vi) prediction of transfused survivability of RBCs;
  b) detecting a signal or light reflected off the surface of the array under conditions effective to identify any target molecules bound thereto, thereby determining the presence and quantity of said target molecules within said blood sample;
  c) determining, based on said light reflection or signal data, whether a target molecule is present or absent from the tested blood sample; and
  d) determining quantitative and measurable blood quality based on the above determinations, wherein said quantitative and measurable blood quality:
  comprises data regarding: (i) RBCs' deformability; (ii) RBCs' aggregability; and (iii) RBCs' adherence to endothelium
  comprises determination of: blood type, blood sub-group, and identification of contaminating agents
  are based on specific RBCs' characteristics of: deformability, aggregability and adherence to endothelium;
  wherein all of said blood bank tests are designed to be performed simultaneously on the same array of binding molecules; and
  wherein said method enables detection of even picograms of substance and thus enables determination of the presence or absence of a pathogen material within a sample or within RBCs.

2. The method of claim 1, further comprising step (a1) of washing the array to remove materials/molecules un-specifically bound thereto.

3. The method of claim 2, wherein said light detection step comprises
  (i) measuring light reflected from the array and providing an output identifying specifically bound target molecules based on the measured reflected light; and/or
  (ii) measuring color change within the array and providing an output identifying specifically bound target molecules based on the measured change of intensity of the signal.

4. The method of claim 1, wherein measuring the reflected light further comprises capturing an image of at least a substantial portion of the surface of the array.

* * * * *